(12) United States Patent
Farrell

(10) Patent No.: US 11,517,786 B2
(45) Date of Patent: Dec. 6, 2022

(54) ORAL TRAINING APPLIANCE

(71) Applicant: Christopher John Farrell, Helensvale (AU)

(72) Inventor: Christopher John Farrell, Helensvale (AU)

(*) Notice: Subject to any disclaimer, the term of this patent is extended or adjusted under 35 U.S.C. 154(b) by 253 days.

(21) Appl. No.: 16/646,991

(22) PCT Filed: Sep. 13, 2018

(86) PCT No.: PCT/AU2018/050992
§ 371 (c)(1),
(2) Date: Mar. 12, 2020

(87) PCT Pub. No.: WO2019/051545
PCT Pub. Date: Mar. 21, 2019

(65) Prior Publication Data
US 2020/0215384 A1 Jul. 9, 2020

(30) Foreign Application Priority Data

Sep. 13, 2017 (AU) .................................. 2017903725
May 14, 2018 (AU) .................................. 2018901645

(51) Int. Cl.
*A63B 23/03* (2006.01)
*A61F 5/56* (2006.01)
*A63B 71/08* (2006.01)

(52) U.S. Cl.
CPC ............ *A63B 23/032* (2013.01); *A61F 5/566* (2013.01); *A63B 2071/086* (2013.01)

(58) Field of Classification Search
CPC ............ A63B 23/032; A63B 2071/086; A63B 2208/12; A63B 2209/00; A63B 71/085;
(Continued)

(56) References Cited

U.S. PATENT DOCUMENTS 3,871,370 A * 3/1975 McDonald ............... A61C 7/08
128/860
4,304,227 A * 12/1981 Samelson ............... A61F 5/566
128/857
(Continued)

FOREIGN PATENT DOCUMENTS

CN 101119699 A 2/2008
CN 203736331 U 7/2014
(Continued)

OTHER PUBLICATIONS

Google translation of JP2008067732 (retrieved from: https://patents.google.com/patent/JP2008067732A/en?oq=2008067732) (Year: 2008).*

(Continued)

*Primary Examiner* — Jennifer Robertson
*Assistant Examiner* — Catrina A Letterman
(74) *Attorney, Agent, or Firm* — Lathrop GPM LLP

(57) ABSTRACT

An oral training appliance for training the tongue and lips of a person is disclosed. The appliance comprises a U shaped body comprising a front section and two arms, an inner wall and an outer wall. A tongue training member extends from the inner wall and is moveable in response to movement by the user's tongue from a rest configuration to a training configuration. The appliance also comprises a lip training member and is moveable in response to movement of a user's lower lip from a rest configuration to a training configuration and the lip training member is biased towards the rest configuration.

15 Claims, 10 Drawing Sheets

(58) Field of Classification Search
CPC .. A61F 5/566; A61C 7/36; A61C 7/08; A61C 5/007; A61C 7/10; A61C 5/90; A61C 17/10
See application file for complete search history.

(56) References Cited

U.S. PATENT DOCUMENTS

| | | | |
|---|---|---|---|
| 5,779,470 A | 7/1998 | Kussick | |
| 2005/0192157 A1 | 9/2005 | Norton | |
| 2006/0219250 A1* | 10/2006 | Farrell | A63B 71/085 128/859 |
| 2007/0254256 A1* | 11/2007 | Farrell | A61C 7/08 433/6 |
| 2009/0018582 A1* | 1/2009 | Ishikawa | A63B 23/18 606/235 |
| 2010/0184566 A1* | 7/2010 | Munehiro | A63B 21/026 482/11 |
| 2013/0104913 A1* | 5/2013 | Evans | A63B 71/085 128/861 |
| 2014/0130807 A1 | 5/2014 | Hart | |
| 2014/0190490 A1 | 7/2014 | Walker et al. | |
| 2014/0261461 A1* | 9/2014 | O'Donoghue | A63B 71/085 128/861 |
| 2014/0261465 A1* | 9/2014 | Turkbas | A63B 71/085 128/862 |
| 2016/0256762 A1* | 9/2016 | Tucker | A63B 71/081 |
| 2017/0020716 A1* | 1/2017 | Hart | A63B 71/085 |
| 2017/0071701 A1 | 3/2017 | Bergersen | |
| 2017/0112659 A1 | 4/2017 | Akihiro | |
| 2019/0015726 A1* | 1/2019 | Turkbas | A63B 71/085 |

FOREIGN PATENT DOCUMENTS

| | | | | |
|---|---|---|---|---|
| CN | 104434323 A | 3/2015 | | |
| CN | 104688363 A | 6/2015 | | |
| CN | 206355155 U | 7/2017 | | |
| CN | 107613913 A | 1/2018 | | |
| DE | 102007059180 A1 | 6/2009 | | |
| EP | 2848229 A1 | 3/2015 | | |
| JP | 2003-275311 A | 9/2003 | | |
| JP | 2008067732 | * | 3/2008 | ............ A63B 23/03 |
| JP | 2014-110821 A | 6/2014 | | |
| JP | 6017780 B2 | 11/2016 | | |
| RU | 24790 U1 | 8/2002 | | |
| RU | 2340378 C2 | 12/2008 | | |
| RU | 2013138149 A | 2/2015 | | |
| WO | WO 2012/155214 A1 | 11/2012 | | |
| WO | WO 2016/187646 A1 | 12/2016 | | |
| WO | WO 2016187646 A1 | 12/2016 | | |

OTHER PUBLICATIONS

Russian Patent Application No. 2020112806, Office Action, dated Dec. 16, 2021, with English Translation, 33 pages.
Chinese Patent Application No. 201880059800.7, First Office Action dated Apr. 7, 2021, 10 pages.
English Translation of Chinese Patent Application No. 201880059800.7, First Office Action dated Apr. 7, 2021, 10 pages.
Chinese Patent Application No. 201880059800.7, Second Office Action dated Sep. 15, 2021, 10 pages.
Chinese Patent Application No. 201880059800.7, English translation of Second Office Action dated Sep. 15, 2021, 12 pages.
PCT/AU2018/050992 International Search Report and Written Opinion dated Nov. 19, 2018, 13 pages.
European Patent Application No. 18656399, Search and Opinion dated May 10, 2021, 9 pages.
Japanese Patent Application No. 2020-515207 Notice of Reasons for Refusal dated Aug. 22, 2022, with English translation, 15 pages.

* cited by examiner

ORAL TRAINING APPLIANCE

FIELD

This disclosure relates to an oral training appliance that may assist in training and promoting beneficial myofunctional habits. This may assist in creating the most suitable intra-oral environment for achieving correct dental occlusion. It will therefore be convenient to hereinafter describe the invention with reference to this example application. The disclosure also relates to a method of myofunctional training to provide improved oral posture that uses the disclosed oral training appliance.

BACKGROUND

Humans have an upper jaw called a maxilla forming an upper arch and a hinged lower jaw called a mandible forming a lower arch. A person has correct dental occlusion when the upper arch matches the size and shape of the lower arch such that the teeth of the upper and lower jaw come together when the jaws are closed. Further individual teeth of the upper and lower arch are correctly positioned along the length of the arch relative to each other such that they match each other correctly. However while the upper and lower arches are broadly of the same size they are subtly offset relative to each other. Specifically the teeth of the upper arch are off set relative to the teeth of the lower arch so that at least part of each tooth of the upper arch is positioned outward of the corresponding tooth on the lower arch. The incisors of the lower arch are positioned behind the incisors of the upper arch.

However malocclusions which involve a mismatch in the sizes of the upper and lower jaw are a relatively common condition in human populations around the world. In a Class 2 malocclusion, called retrognathism or overbite, there is retrusion of the mandible and the maxilla and teeth severely overlap the mandible and teeth. In a class 3 malocclusion, it is the mandible that is protrusive.

The muscles of the face have important roles in performing orofacial functions such as speech, swallowing and mastication. Orofacial myofunctional disorders (OMD) are disorders of the muscles and functions of the face. There is a delicate equilibrium between the internal force of the tongue on the teeth and the associated maxilla and mandible and the external forces of the lip and cheek muscles. Any disturbance of such equilibrium as a result of OMD can have significant effects on facial skeletal growth and development.

Thus, poor oral posture, bad oral habits, such as thumb sucking, tongue thrusting and non-nutritive sucking in a child with growing skeleture, can cause a number of problems such as malocclusion, crowding of the teeth, an open bite and narrow arch formations.

In the present specification, the terms "correct oral posture" or "correct oral habits" includes one or more of the correct placement of the tongue on the upper palate, a competent lip seal, a correct swallowing pattern in which the tongue is in the correct position, and there is a correct swallow which means the swallow does not involve use of the muscles of the cheeks, lips or chin and nasal breathing.

In the present specification, the terms "bad oral habits" or "poor oral posture" includes one or more posture or habits that are not correct and include a tongue that is not in the correct position, tongue thrusting, digit sucking, an incompetent lip seal, an incorrect swallowing pattern and mouth breathing.

The conventional orthodontic approach to the failure to treat these problems at an early age in a growing child is physical intervention such as braces and/or surgery at a later date. This is a most undesirable outcome for a child or young adult.

An alternative and certainly less invasive approach is the use of intra oral functional appliances that are designed to manipulate the disturbed internal/external force equilibrium so as to allow the bones and teeth to grow normally.

Habitual mouth breathing and/or poor oral posture are OMDs that can have significant adverse effects. When the tongue is in the natural resting position, the tip positions on the incisal papilla at the anterior part of the upper palate. With the tip of the tongue in this position, the dorsum of the tongue runs at the cervical third of the crowns and roots of the upper premolars. The base of the tongue goes downward at the molars, leading to insert at the hyoid bone. When the tip of the tongue is at its physiological position, its dorsum and base tend to reposition at their physiological positions as well, with the base descending at the molar area. This position is important as it is the tongue that guides growth of the maxilla by virtue of the correct position.

However, when mouth breathing, the tongue is in a lowered position to allow the child or person to more easily breathe through the mouth. This allows the buccinators to push inward on the maxilla, thereby adversely affecting its development. As the lateral wall of each nasal cavity mainly consists of the maxilla, the nasal cavity will be reduced, thereby adversely affecting nasal breathing.

Children with mouth breathing have atypical facial features: long face, dark circles, narrow nostrils, transverse contraction of the upper jaw, high arched palate and gummy smile associated with malocclusion of class II or, sometimes, class Ill, with a high prevalence of posterior crossbite and anterior openbite.

A class 2 malocclusion and a skeletal Class 2 profile with increased overjet can develop in children who mouth breath and rotate the mandible in a posterior and inferior direction. The muscles which depress the jaw to open the mouth exert a backward pressure upon the mandible which displaces the mandible distally and retards its growth. The buccinator muscles are made tense by opening the mouth and tend to exert lingual pressure on the maxillary bicuspids and molars, which do not receive sufficient support from the tongue, so that the palate and the upper dental arch becomes quite narrow. Lip function is abnormal, the lower lip being large and bulbous and the upper lip short and functionless, with often lower lip forced up under the upper incisor, that are further protruded with increased overjet (the measurement between the upper incisal edge and the labial surface of the lower incisors).

Mouth breathing also may have a role in the development of some forms of Class 3 malocclusion. Mouth breathing children have a constantly open jaw and a low posture of the tongue that may contribute to excessive mandibular growth, with constant distraction of the mandibular condyle from the fossa which may be a growth stimulus. In addition, the lack of thrust of the tongue on the palate and on the upper jaw may cause a sagittal and transverse maxillary skeletal deficit, with reduced or reverse overjet.

The high prevalence of narrow dental arches generally results in dental crowding, especially on the maxilla.

Mouth breathing in adults can also have adverse effects and is associated with sleep disorder breathing (SDB), including snoring and obstructive sleep apnea (OSA). Mouth breathing is also associated with hyperventilation syndrome (HVS).

Incorrect tongue position also occurs with other oral habits such as digit sucking, non-nutritive sucking and tongue thrust.

A still further effect of low tongue position is incorrect swallowing. Negative pressure or suction in the mouth is required to swallow. The normal swallow occurs when the teeth are kept together with an adequate lip seal. The tongue is pressing in the upper palate to create suction. The tongue moves across the upper palate to increase suction. There is a reciprocal action between the tongue and the lips during the increased suction of the swallow. This movement of the tongue also puts a widening, forward and upwards force on the maxilla that is beneficial for facial development.

On the other hand, during the incorrect swallow, the teeth are slightly apart with the tongue placed between them, providing an inadequate seal. Because the seal is inadequate, the lips, cheeks and chin muscles are used as compensation which sucks against the dentition, thereby putting further forces on the face and palate. This can cause overdevelopment of the buccinators muscle, thereby providing more constrictive force on the maxilla. It also results in overactivity of the mentalis (muscle of the chin).

As mentioned above, functional appliances may be used to correct malocclusions, by operating to return the equilibrium of the mismatched forces caused by the OMD. In the 1950's Rolf Frankel developed a functional appliance (now known as a Frankel appliance) that allowed the maxillary and mandibular muscles to play an important part in an orthodontic treatment and to restrict undesirable forces.

However, a functional appliance, on its own, whilst correcting a malocclusion, does not necessarily retrain the tongue and orofacial muscles for proper oral posture. One reason is that the tongue and orofacial muscles have been trained to function in a disordered manner, or in other words, the disordered function has become a habit. Lack of proper swallowing may cause atrophy and weakness of the tongue.

A habit is an action or condition which by repetition has become spontaneous. Abnormal oral habits operate so quietly and unconsciously that even the patient is frequently unaware of their existence. All such simple habits at first are performed by conscious effort. With each repetition it becomes less and less conscious effort and strictly applicable only to motor responses. Finally it is performed entirely unconsciously, becoming a part of the routine of the mind from which the consciousness is removed.

Thus, when the appliance is not being worn, the patient will resume disordered oral posture. Often the lip muscles have become weaker and are unable to maintain a lip seal. This is known as lip incompetence. The tongue returns to the lower position in the mouth. If the patient is a habitual mouth breather, they will continue to mouth breathe.

Thus in order for the OMD to be properly addressed, the tongue and lips must therefore be retrained. This is known as myofunctional therapy. Myofunctional therapy is therefore an important adjunct to treatment with a functional appliance.

It will be appreciated therefore, that such retraining of a bad oral habit requires considerable myofunctional therapy and patient compliance is critical. However, any physical therapy, including myofunctional therapy is only as good as a patient's compliance.

Examples of myofunctional lip exercises to encourage a proper lip seal include causing the patient to stretch the upper or lower lip over the other of the lower or upper lip. Another exercise is performed by tightly closing the lips together that helps to increase competency. Another exercise is known as the "button pull" exercise in which a thread is passed through a button and the patient is asked to place the button behind the lips and resist the button from being pulled away using lip seal.

There are also a number of appliances that have been proposed to strengthen lips and facial muscles. One such device is known as an "oral screen" that has a curved member that rests between the lips and the teeth with a holding ring or cord extending out between the lips. The screen when worn prevents tongue thrust and mouth breathing. The screen can also be used for therapy by using the lips to resist removal of the screen by pulling on the holding ring or strap.

There are numerous other devices that allegedly exercise the lips and facial muscles. Many devices have members that are biased in an open position that is placed in the mouth and the person is instructed to close the lips together against the bias. Many such devices and associated exercises are primarily concerned with toning or firming the facial muscles and improving blood flow to the lips to provide an alleged cosmetic effect.

On the other hand, myofunctional therapy is concerned with training muscles to attain the proper form for promoting a lip seal, palatal tongue rest position, and nasal breathing. Those exercises and devices used for cosmetic purposes are not concerned with muscle training to correct poor oral posture and proper palatal tongue position is not a consideration.

Turning now to myofunctional tongue exercises, a common exercise is known as the 4S exercise that includes (1) identifying the correct palatal position or "spot", (2) placing the tongue on the spot which stimulates the salivary glands, (3) squeezing the tongue with the teeth closed against the "spot" followed by relaxing and (4) swallowing with the teeth together and tongue tip on the "spot". It is recommended to practice this exercise at least 40 times a day. It will be appreciated that compliance is critical to this exercise and for children relies heavily on parental supervision. It is also not possible for a parent to ensure that the exercise is being carried out correctly.

There are also intraoral appliances that have guides for guiding the tongue into the correct position or provide barriers to tongue thrusting. In practice, these appliances do nothing to train the tongue in the correct position, nor strengthen the muscles of the tongue so as to maintain the correct position and have sufficient strength for normal swallowing.

It will be appreciated that there is a constant desire in the field of orthodontics and myofunctional therapy to provide new appliances and treatment methods that can provide patients with alternatives to existing appliances and treatments and that may provide a different or better outcome for a patient.

SUMMARY

According to one aspect of the disclosure there is provided an oral training appliance for training the tongue and lips of a user, the oral training appliance comprising;
- a U shaped appliance body comprising a front section and two arms, the appliance body comprising an inner wall and an outer wall;
- a web interconnecting the inner wall and the outer wall so as to define an upper dental arch receiving channel;
- a tongue training member configured in use to extend posteriorly from the inner wall and locate above the tongue and that is moveable in response to upwards movement by the user's tongue from a rest configuration to a training configuration and the tongue training member is biased towards the rest configuration; and a lip training member extending forwardly of the front section and is configured in use to extend between the user's lips, and is moveable in response to movement of a user's lower lip from a rest configuration to a training configuration and the lip training member is biased towards the rest configuration.

As mentioned above, there is an art acknowledged difficulty with patient compliance when a patient is being treated with myofunctional therapy to correct bad oral habits. This is particularly pertinent to children who have a short attention span. Functional appliances on their own, whilst being able to shield the underlying growing structure from deviant performance of the facial muscles, do not serve to retrain the lips and tongue and correct an incorrect swallow. Without such training, after discontinuance of functional appliance therapy, poor oral posture will regress that therapy.

The present inventor has also appreciated that lip exercises using art known appliances, on their own, does not automatically result in a competent lip seal. This is because it is also important for a proper lip seal that the tongue is in the correct palatal position so as to provide the necessary degree of suction. Still further, if the tongue is in the incorrect position during swallowing, the necessary suction for swallowing cannot be created by the tongue and must be compensated for by the buccinators and mentalis.

The oral appliance body is suitably manufactured from a soft and/or resilient material, suitably a thermoplastics material.

The oral appliance body, and in particular the arms suitably has a degree of compliance such that the oral appliance can be fitted to users with different size dental arches.

The thermoplastics material may soften at temperatures below 100° such that it is user mouldable. Such materials include ethylene vinyl acetate (EVA) that allows a user to soften the device in hot water and mould the device about the user's teeth as is well known with mouth guards.

In this case, the oral apparatus may also have a core or frame from material that does not soften below 100° C. for example a polyolefin such as polyethylene or polypropylene) so as to provide structural support to the appliance.

Alternatively the oral appliance may be formed from a soft thermoplastics material that does not soften below 100° soft polymer but is soft and compliable at room temperature such as polyurethane, liquid silicon rubber or silicone.

Silicone, polyurethane and liquid silicone rubber are particularly suitable as they are pliable and do not require moulding to a user's teeth. This may improve comfort; allow the user some jaw movement that will also contribute to user comfort and thus compliance.

Suitably the oral appliance may be made by injection moulding.

The appliance body may be made in a number of different stock sizes so that a majority of the population can select an appliance that can be fitted over their upper arch with a reasonable fit.

The disclosed training appliance suitably has both upper and lower dental arch receiving channels. When the appliance is fitted into a patient's mouth, the mandible must be positioned so that the lower dental arch is received within the lower dental arch receiving channel. If a person is a mouth breather, the mandible is often lowered to facilitate mouth breathing. Thus wearing the appliance will encourage such a patient to raise the mandible.

Further, the upper and lower dental arches of the appliance may be aligned with respect to each such that when worn the upper and lower dental arches of the patient may be in or close to correct occlusion. For example if the patient has a class 2 malocclusion, the upper and lower dental arch receiving channels may be configured for mandibular advancement.

The disclosed appliance has a tongue training member configured in use to extend posteriorly from the inner wall and locate above the tongue.

The tip of the tongue is highly sensitive and haptically explores objects in the mouth and provides perception of size and shape of objects in the mouth. This is important for mastication and swallowing. The presence of the tongue training member in the mouth will generally evoke a spontaneous response for the tongue to find its way towards to touch and explore the tongue training member. This will create a stimulating effect and encourage a fuller flow of blood to the tongue. This spontaneous response assists in transforming correct tongue placement from a conscious to an unconscious level.

The tongue training member has a rest configuration and a training configuration and is biased towards the rest configuration. By training configuration is meant any configuration in which the tongue training member has been moved to from the rest configuration by the action of the tongue.

The tongue training member can be moved from the rest configuration to the training configuration by upwards movement of the tongue on the tongue training member against the bias towards the rest position. This works the muscles of the tongue and in particular the genioglossus (the extrinsic tongue muscle that forms the majority of the tongue body and which is attached to the mandible).

Tongue strength may be measured by a number of art known techniques. An example is a tongue strength measuring device available from IOPI Medical. Typically a pressure measuring device, such as an air-filled bulb is located at the top of the mouth and the patient is asked to elevate the tongue against the device as "hard as possible". The maximum pressure that can be obtained is an evaluation of tongue strength. Generally, maximum tongue pressures of between 37 kPa to 44 kPa are considered to correlate with abnormally low tongue strength. The average tongue strength of the population is in the order of 60 kPa to 70 kPa.

As the tongue training member is biased towards the rest configuration, the tongue training member can move between the rest and training configurations by tongue movement. This can stimulate the salivary gland on the base of the tongue and can also increase the suction within the oral cavity. The suction may also assist in creating a lip seal as will be discussed below.

The tongue training member may be any suitable shape and/or configuration that allows for upward movement of the tongue and is biased towards the rest configuration.

Suitably, the tongue training member extends posteriorly from the upper part of the inner wall of the appliance.

Suitably, the tongue training member is a resilient plastics material formed integrally with the appliance body and the bias is provided by elastic deformation of the plastics material.

It will be appreciated that the elastic limit of the plastics material is desirably greater than maximum tongue pressure of the normal population (about 60 kPa to about 70 kPa).

In one aspect, the tongue training member comprises a tab like member and a connecting member for connecting to the inner wall by a hinge part. Upwards movement on the tab by the tongue causes elastic deformation around the hinge part. In this aspect, when the tag member is in the rest configuration it is spaced a distance below the person's hard palette.

Upward movement of the tongue on the tab member pushes the tab member towards the person's upper palette. As the person's tongue become stronger, the maximum available deformation of the tongue training member should increase. Suitably when the person's tongue has achieved a maximum tongue pressure corresponding with that of the general population, the top surface of the tab member may abut or contact the upper palette, thereby providing a positive feedback to the user.

Suitably, the upper surface of the tongue training member is shaped for compatibility with the upper palate for comfort.

Suitably, the lower surface of the tongue training member is concave so as to define a surface for comfortable receipt of the tip of the tongue.

The tongue training member may be integral with the oral training appliance body, in which case may be moulded from a plastics material in one piece. Alternatively the tongue training member may be formed separately and joined thereto, for example in a two step moulding process. In this way, the tongue training member may be formed from a plastics material with different physical properties than the body for example in terms of resilience, flexibility or the like.

The tongue training member may be a solid compressible resilient member, such as a rubber material.

The tongue training member may be a hollow compressible resilient member.

Suitably, the tongue training member has an upper wall, a lower wall that define a cavity or a transverse through hole there between. The cavity and through hole may receive excess saliva, generated by stimulating the tongue during tongue exercises.

In another embodiment the cavity has an opening facing in the posterior direction. The cavity may be configured to receive the tip of a user's tongue when resting between exercises. In this way the tongue is kept in the correct position.

In another embodiment, the tongue training member may be a solid member formed from a plastics material having shape memory that deforms to the training configuration and returns to the rest position when tongue pressure is released.

The appliance also has a lip training member extending forwardly of the outer wall and has a rest configuration and a training configuration such that when worn, the lip training member extends between the user's lips.

The lip training member has a rest configuration and a training configuration. By training configuration is meant a configuration in which the lip training member has been moved from the rest configuration by the action of the lips.

Suitably the lip training member has an upper surface and a lower surface and is configured such that in use the lower surface is moveable in response to upwards movement of a patient's lower lip from the rest position to a training configuration and the lip training member is biased towards the rest position.

The lip training member may be integral with the training appliance body, in which case the appliance may be moulded from a plastics material in one piece. Alternatively the lip training member may be formed separately and joined to the appliance body. The lip training member may be formed from a plastics material with different physical properties than the body for example in terms of resilience, flexibility or the like.

The lip training member may be a solid compressible resilient member.

The lip training member may be a hollow compressible resilient member.

In one aspect, the lip training member has an upper wall, a lower wall and a transverse through hole there between.

As mentioned above, if the patient is a habitual mouth breather, the mandible will normally be lowered at rest. In order to engage the lower dental arch receiving channel of the appliance, the patient will have to raise the mandible so as to retain the appliance in the mouth. This immediately raises the lower lip.

Suitably the lip training member is configured such that when the mandible is moved such that the lower dental arch is received within the lower dental arch receiving channel, the lower lip is in contact with the lower surface of the lip training member, or sufficiently close to the lower surface, such that the lower lip can be raised to touch the lower surface of the lip training member without undue strain of the mentalis. Mouth breathers when trying to close their mouth generally compensate by using the mentalis to raise the lower lip thereby causing strain on this muscle.

Suitably, the upper lip will be in contact with the upper surface of the lip training member. Such lip contact may stimulate the lips, increase blood flow and create a spontaneous response to move the lips with respect to the lip training member.

The user will be instructed to urge the lips together. This will generally require a greater degree of upward movement of the lower lip than downward movement of the upper lip. Upwards movement of the lower lip moves the lip training member against the bias to the rest configuration. This movement tones and strengthen the lips whilst at the same time, the tongue is in the correct position.

It will be appreciated that the presence of the appliance in the mouth will provide a clear feedback and spontaneous response may promote compliance. A person does not need to "find the spot" with the tongue as this will naturally happen in response to the tongue training member in the mouth.

Further a combined tongue movement on the tongue tag can promote a suction as the patient is doing the lip closure exercise. The suction will facilitate lip seal.

Suitably, the appliance also has a lip bumper that discourages an overactive mentalis that is often observed in patients with a class 2 malocclusion. The lip bumper is suitably in the form of one or more projections that touch the mucosa of the lip and inhibits overactivity of the mentalis muscle. The lip bumper may comprise a plurality of dimple like protrusions on the buccal surface, e.g. arranged in the form of an array.

The user may be instructed to swallow with the lips together about the lip training member, the mandible in the correct position and the tongue in position against the tongue training member, thereby assisting in a correct lip seal. In other words, the person has correct oral posture for a correct swallowing pattern. As discussed above, during the swallow suction within the mouth is increased by the action of the tongue. As a result of the reciprocal action between tongue and lips, this exercise may assist in training and strengthening the lips towards forming a competent lip seal.

As mentioned above, where there is an inadequate lip seal and improper tongue position the person compensates for inadequate seal by using lip, chin and cheek muscles to suck against the dentition to provide the necessary suction from swallowing. However, the use of lip muscles to suck in the cheeks is prevented by the buccal surface of the outer wall. Activity of the mentalis is reduced by the lip bumper.

Pressing the lips together to form a seal is not necessary as the necessary suction is provided by the tongue being in the correct raised position.

In other words, when wearing a training appliance as disclosed and activating the tongue and lips, a person can only swallow with a correct swallowing pattern. By consciously performing a correct swallowing pattern a number of times a day, the correct swallowing pattern will become habitual.

The appliance body may be made in a number of different sizes and the sizes may be selected so that a majority of the population can select an appliance that can be fitted over their upper arch with a reasonable fit. Typically there may three to four different sizes of the appliance body.

The oral training appliance may be used as an alternative or adjunct to conventional oral myofunctional therapy to promote correct oral posture. Suitably the patient will be asked to wear the appliance about 2 to 10 times per day and any intermediate times there between for periods of between 5 to 30 minutes. When worn, the patient will be instructed to practice compressing the tongue training member, generating excess saliva, swallowing with the tongue in position. The patient will also be instructed to practice compressing the lip training member either separately or in conjunction with manipulation of the tongue training member.

The oral training device may be used by a child showing bad oral habits before, or in the early stages of those habits causing adverse dental and/or skeletal changes.

Thus there is also disclosed a method for training good oral habits in a person, comprising providing an oral training appliance as disclosed herein and causing the person to wear the appliance whilst actuating the tongue training member with the tongue and actuating the lip training member with the lips.

The user may be instructed to swallow with the lips together about the lip training member, the mandible in the correct position and the tongue in position against the tongue training member, thereby assisting in a correct lip seal.

The user may be instructed to independently move the tongue and lip training members from the rest to the training configurations.

For persons, and in particular growing children, who have developed or beginning to develop adverse dental and/or skeletal changes, the disclosed oral training appliance may be used as an adjunct to functional myofunctional appliance therapy. The functional appliances are typically worn over night and for a few hours each day. The disclosed oral training appliance may be used for training purposes during those periods of time when the functional appliance is not being worn.

Thus the above method may further may form part of a myofunctional therapy by causing a user to wear a functional oral appliance for a period of time, suitably overnight and using the disclosed oral appliance periodically during the day and conducting lip and tongue strengthening exercises.

It would be considered a beneficial outcome if the patient's oral habits have been retrained before or at the same time as treatment with the functional appliance is completed.

In an alternative arrangement, the lip training member may define a breathing passage in communication with a hole in the front of the appliance body through which the patient can breathe when in the rest position. This variation may be suitable for a person who is a habitual mouth breather and who is gradually learning to nasal breath. Such a person may be an adult with otherwise normal or close to normal occlusion and whose habitual mouth breathing during sleep can present as snoring and/or sleep apneic episodes. When the tongue is in the lower position during sleep, the muscles relax and the tongue can fall backwards and partially or fully block the pharynx.

This does not occur when nasal breathing in which the tongue is in the correct forward position that keeps the airways clear. Thus, the disclosed appliances may also be used by an adult who may have normal occlusion and dentition to train the adult to relocate the tongue in the correct position, to retrain the lips to form a lip seal and promoting nasal breathing.

Where an adult suffers from snoring, apneic episodes or SDB, an appliance may be worn at night whilst sleeping. As discussed above, the tongue will naturally find the correct palatal position that immediately brings the back of the tongue forward and away from the airway. In order to further open the airway, the appliance may be configured to provide a degree of mandibular displacement so as to bring the tongue further forward.

If the person is a habitual mouth breather and normally breathes through their mouth whilst sleeping it is desirable that the appliance can provide for at least some mouth breathing. Whilst many people that are not experts in SDB, promote the use of mouth guards or tape to prevent mouth breathing and to force nasal breathing, those of skill in the art warn against it due to the potential of making it harder to breath. A habitual mouth breather will automatically revert to mouth breathing when asleep. If they are unable to do so, this can create a suffocating feeling and panic. A worst case scenario is that a person may stop breathing.

Further, a person may have compromised nasal passages that inhibits the amount of air that can be breathed through the nose.

Suitably, the lip training member defines a breathing passage that communicates with a breathing hole in the web of the appliance. Whilst the person is asleep, the bias of the lip training member keeps the breathing passage open with the person's lips resting on the upper and lower surfaces of the lip training member.

The person will wear the device for period through the day for tongue, lip and swallowing exercises. In this arrangement, conscious actuation of the lip training member when awake by the lips may compress the lip training member to reduce or even close off the cross sectional area of the breathing passage. This can assist in gradually getting the person to get used to breathing through the nose.

As mentioned above compliance is a well recognised difficulty with conventional oral myofunctional exercise. In the present oral training device, the presence of the device in the mouth actually stimulates the tongue and lip to move to the correct positions at the same time.

Tongue strength may also be compromised by injury, neurological disease or with age. Weakened tongue muscle causes a variety of problems in the oral and pharyngeal phases, making normal swallowing difficult.

The present oral appliance may therefore find application for tongue strengthening exercises with a view to improving swallowing without providing for lip exercises.

Thus in another aspect there is disclosed an oral training appliance comprising a U shaped appliance body comprising a front section and two arms, the appliance body comprising an inner wall and an outer wall;

a web interconnecting the inner wall and the outer wall so as to define an upper dental arch receiving channel;

a tongue training member configured in use to extend posteriorly from the inner wall and locate above the tongue and is moveable in response to upwards movement by the person's tongue from a rest configuration to a training configuration and the tongue training member is biased towards the rest configuration.

There is also disclosed a method of tongue strengthening therapy comprising providing an oral training appliance as disclosed herein and causing a user to wear the appliance periodically whilst causing the tongue training member to move between the rest and training configurations by movement of the tongue.

Suitably tongue strength will be periodically monitored during the treatment.

DETAILED DESCRIPTION

An oral training appliance in accordance with this disclosure may manifest itself in a variety of forms. It will be convenient to hereinafter describe several embodiments of the invention in detail with reference to the accompanying drawings. The purpose of providing this detailed description is to instruct persons having an interest in the subject matter of the disclosure how to carry the invention into practical effect. However it is to be clearly understood that the specific nature of this detailed description does not supersede the generality of the preceding broad description. In the drawings:

Figure 1:
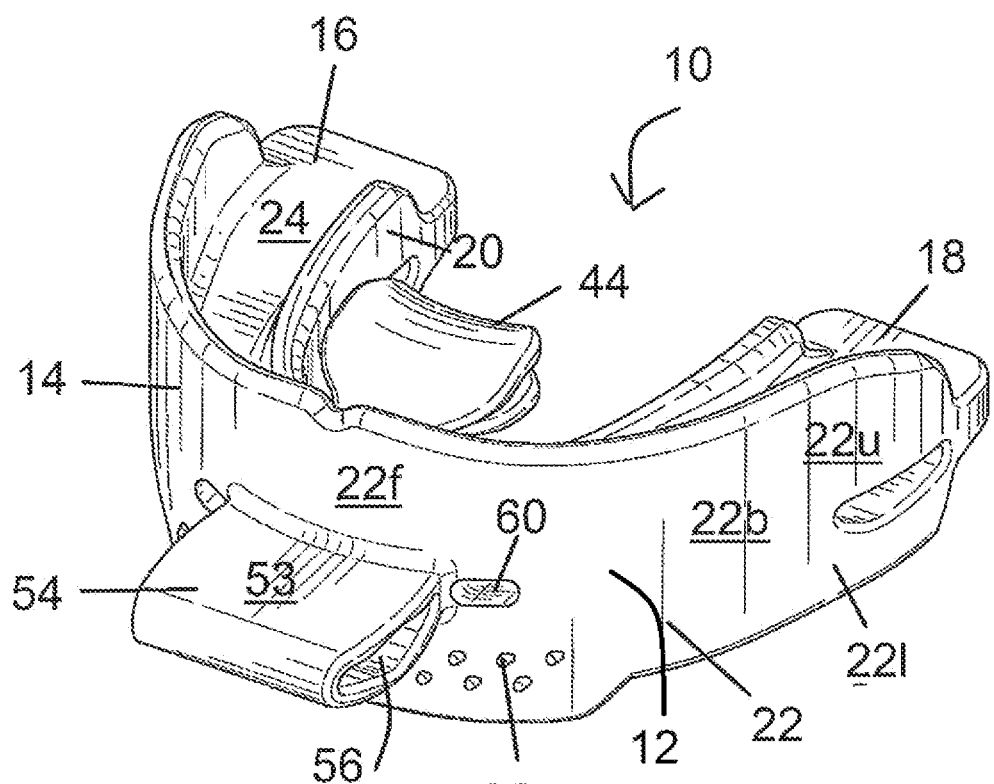
FIG. 1 is front perspective view of an oral training appliance in accordance with one embodiment of this disclosure.
Figure 2:
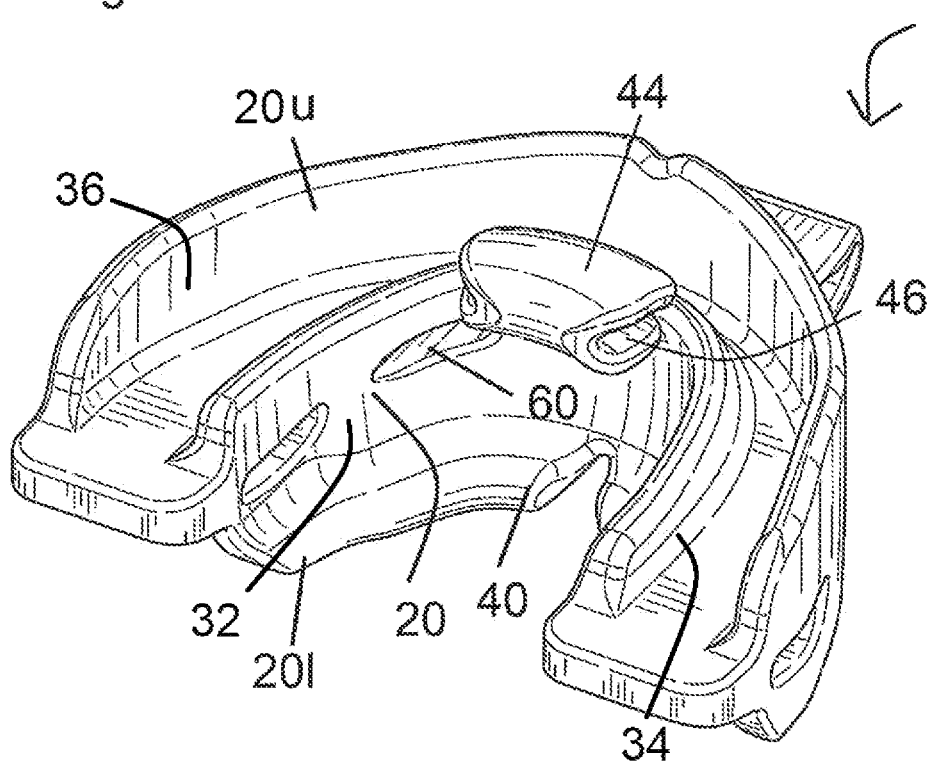
FIG. 2 is a rear perspective view of the appliance of FIG. 1.
Figure 3:
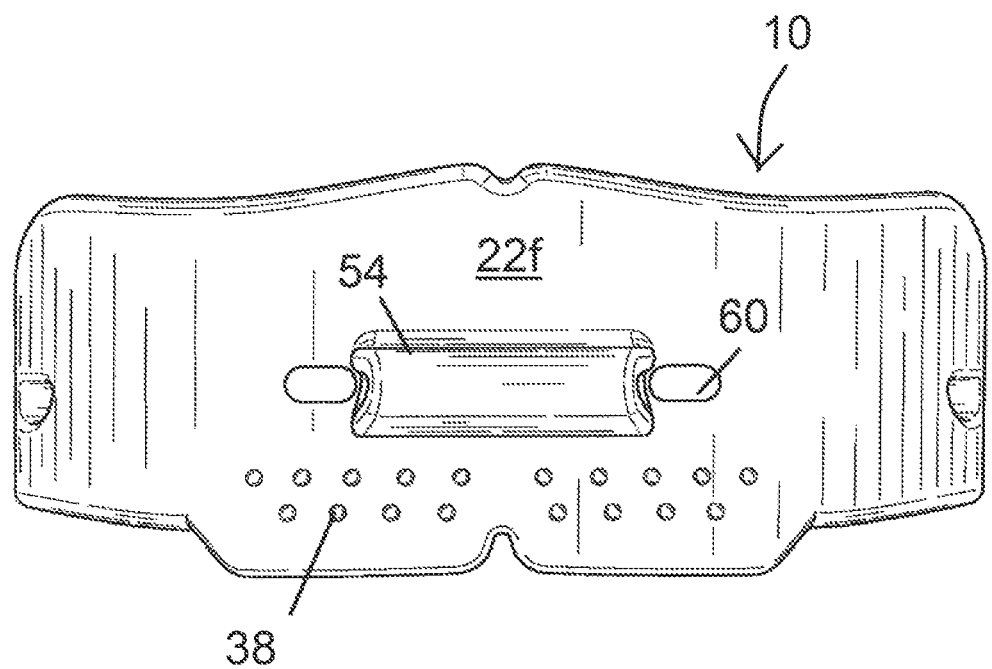
Figure 4:
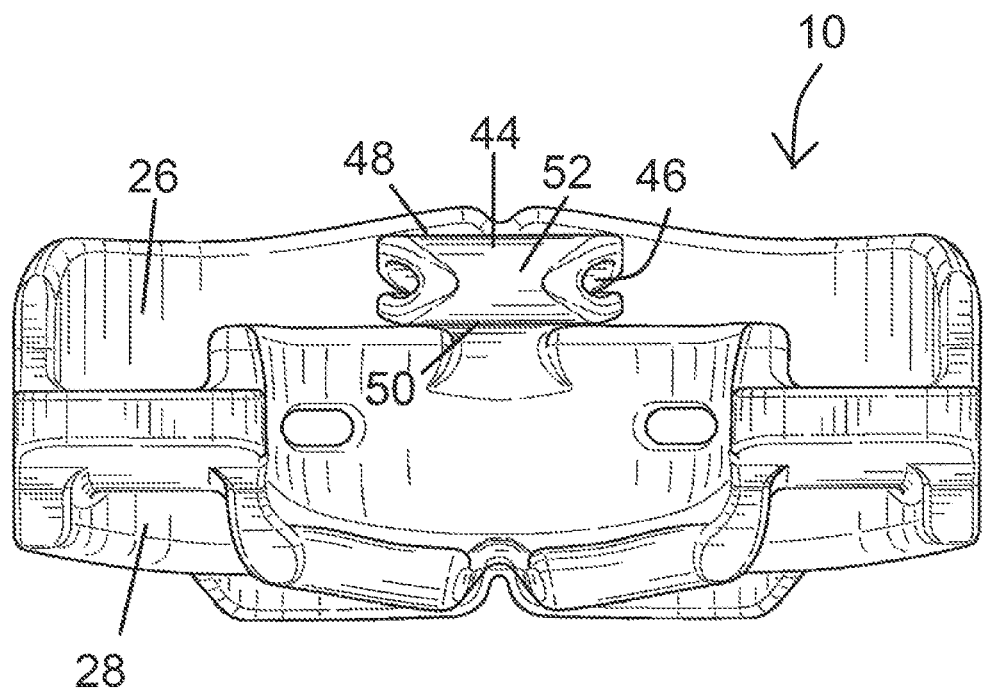
Figure 5:
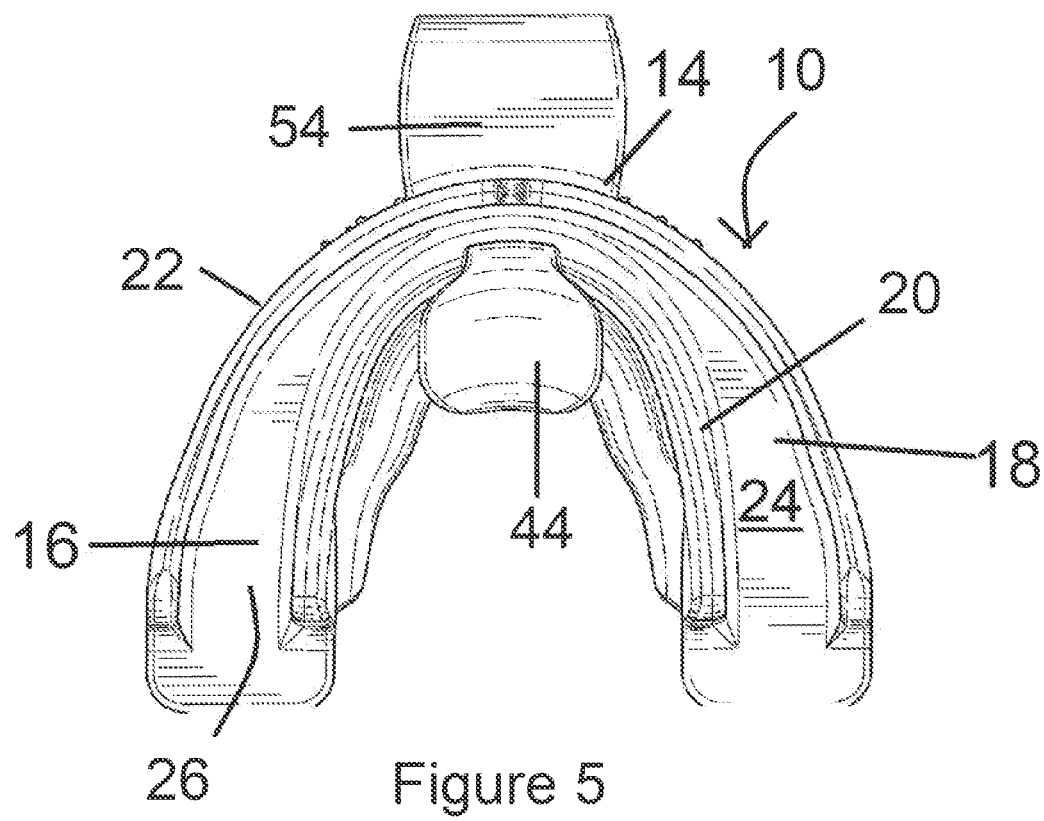
Figure 6:
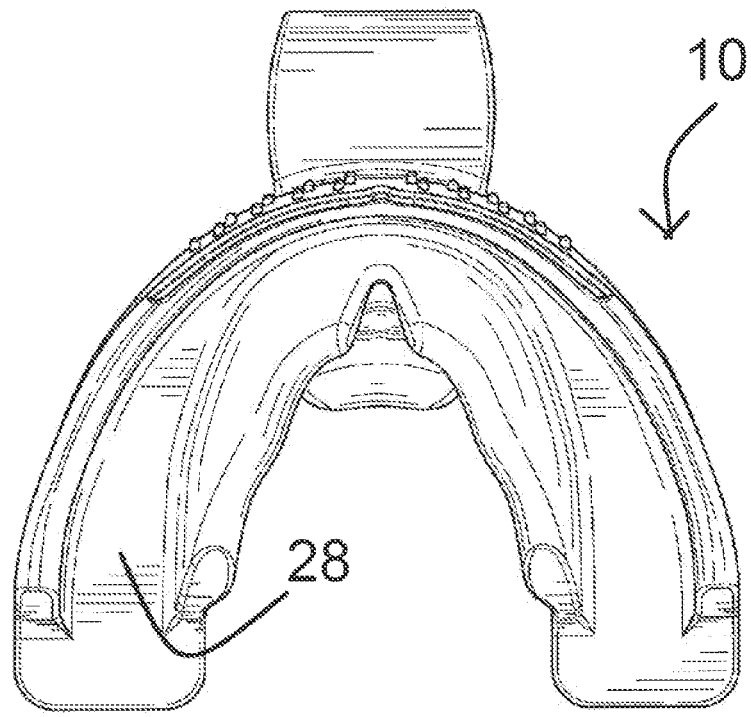
Figure 7:
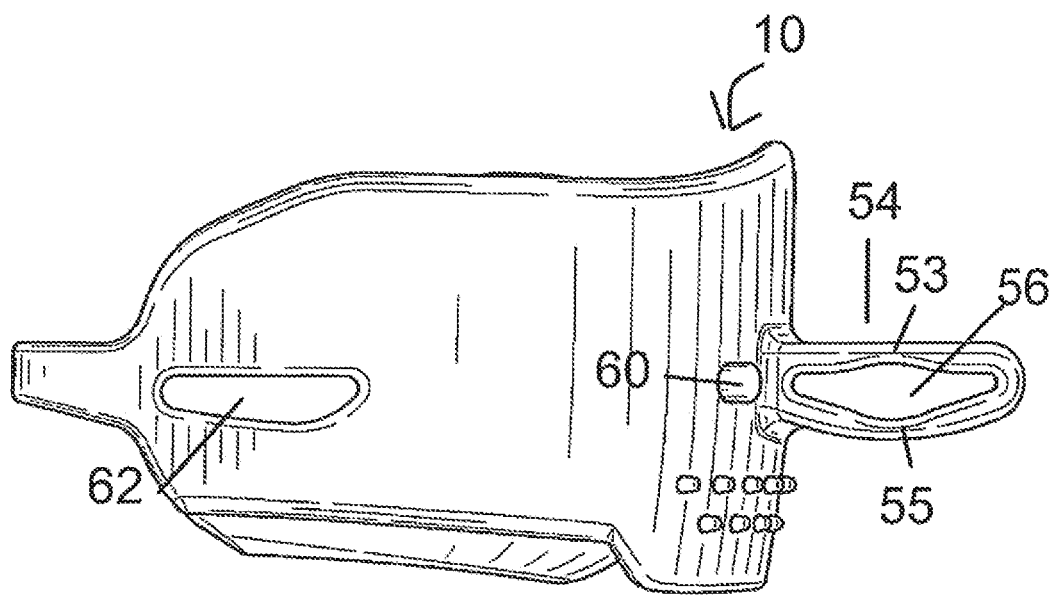
Figure 8:
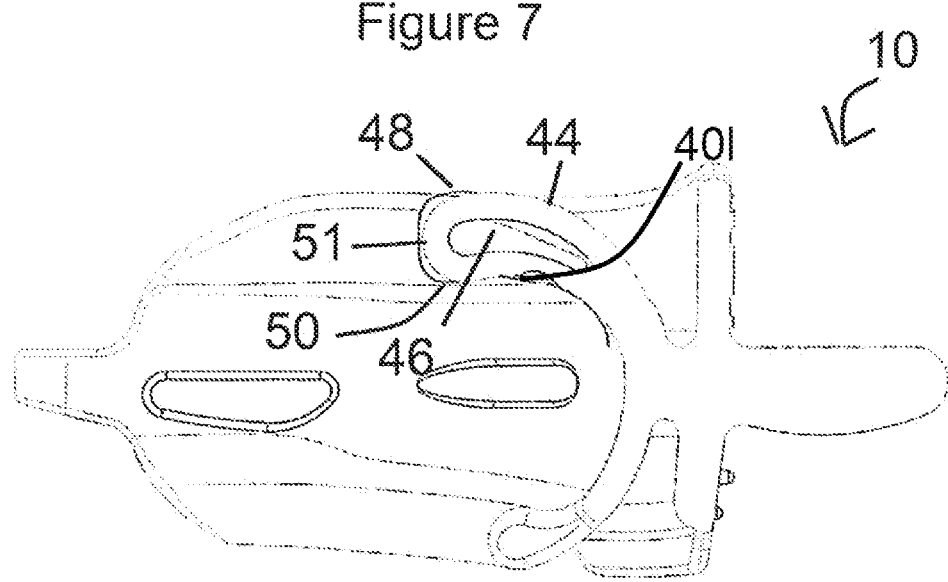
Figure 9:
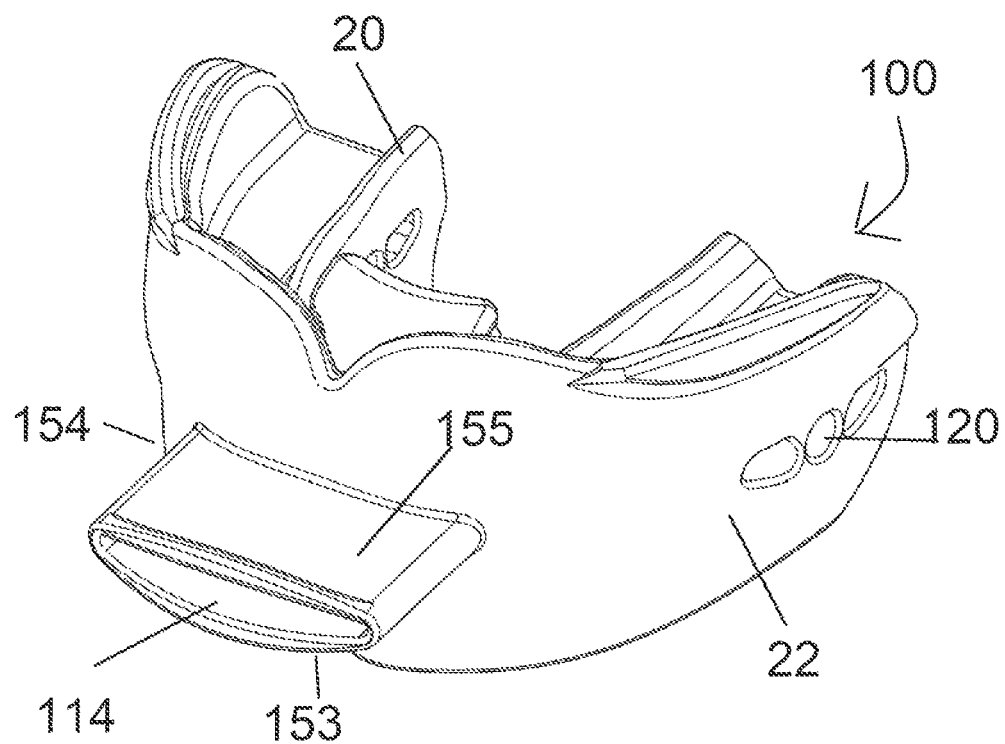
Figure 10:
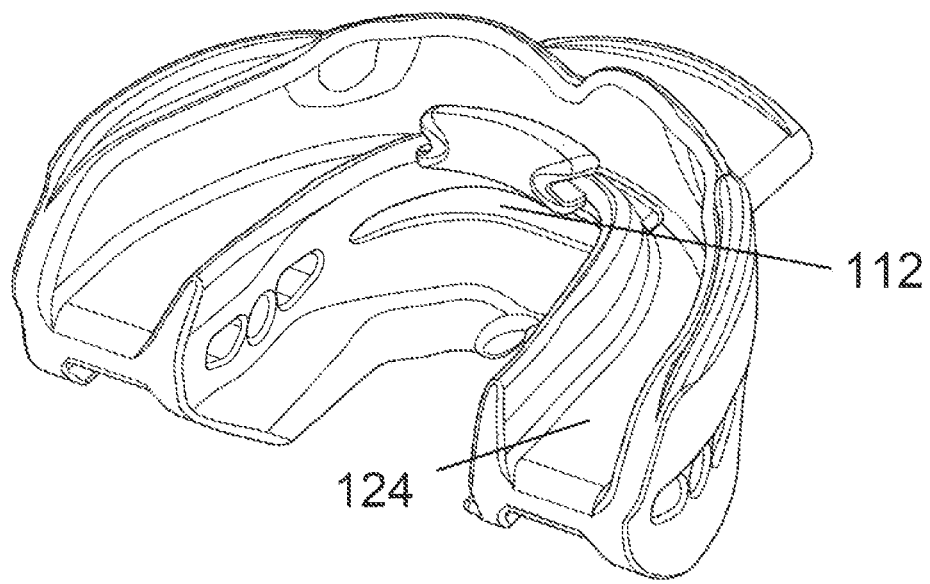
Figure 11:
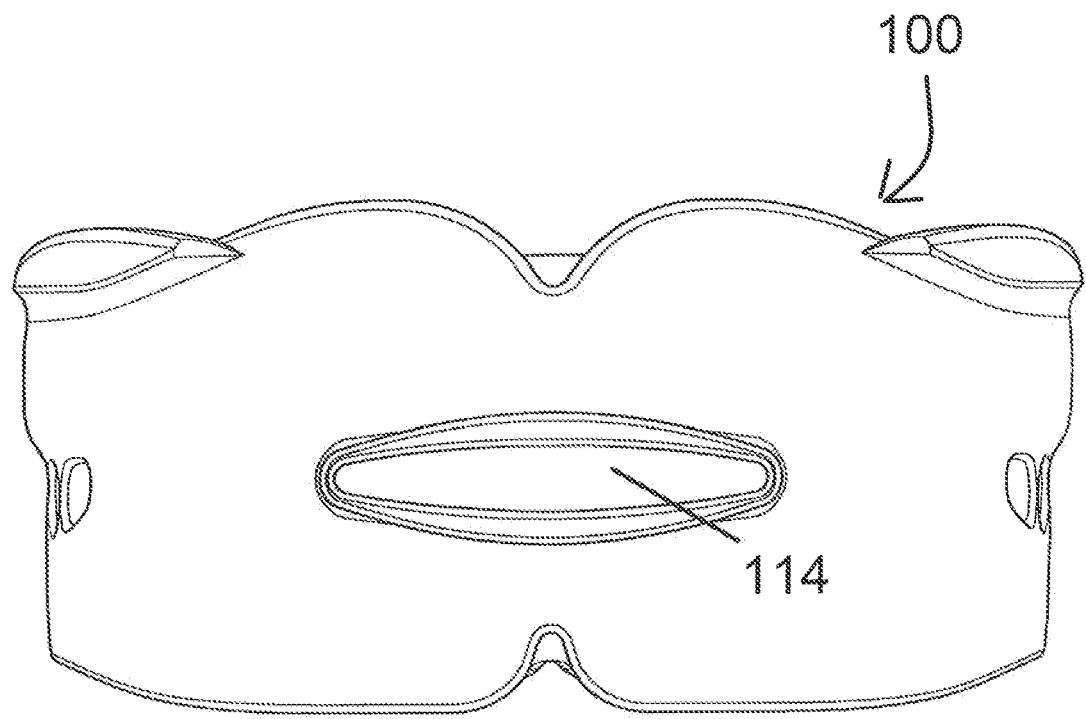
Figure 12:
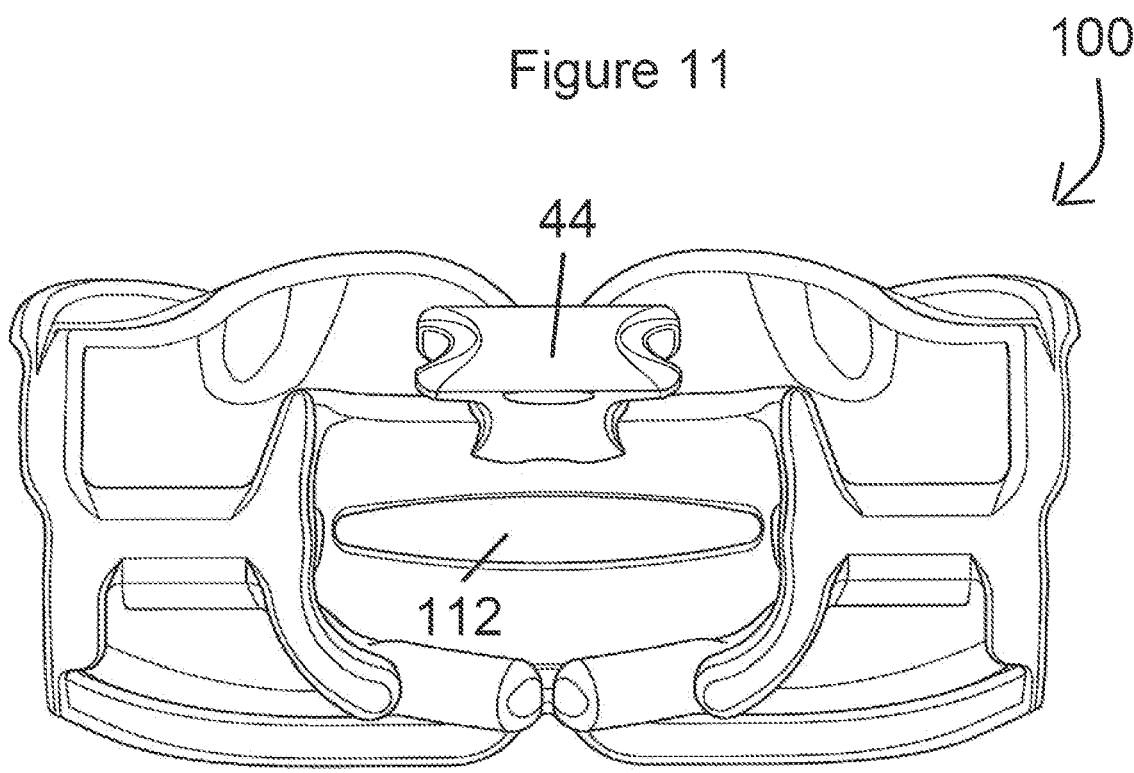
Figure 13:
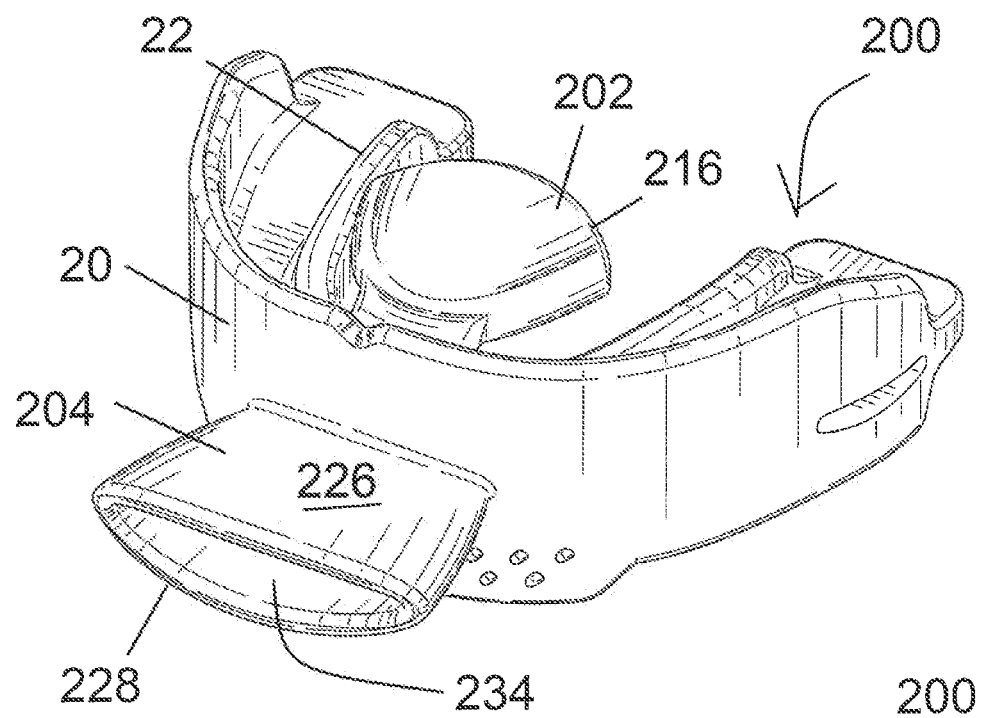
Figure 14:
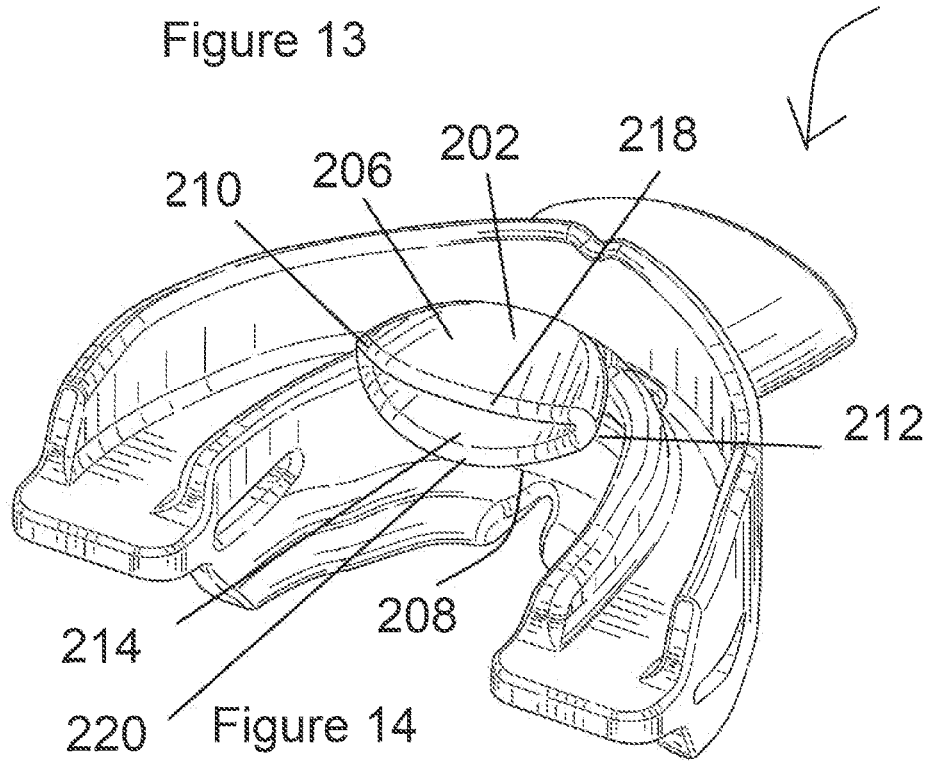
Figure 15:
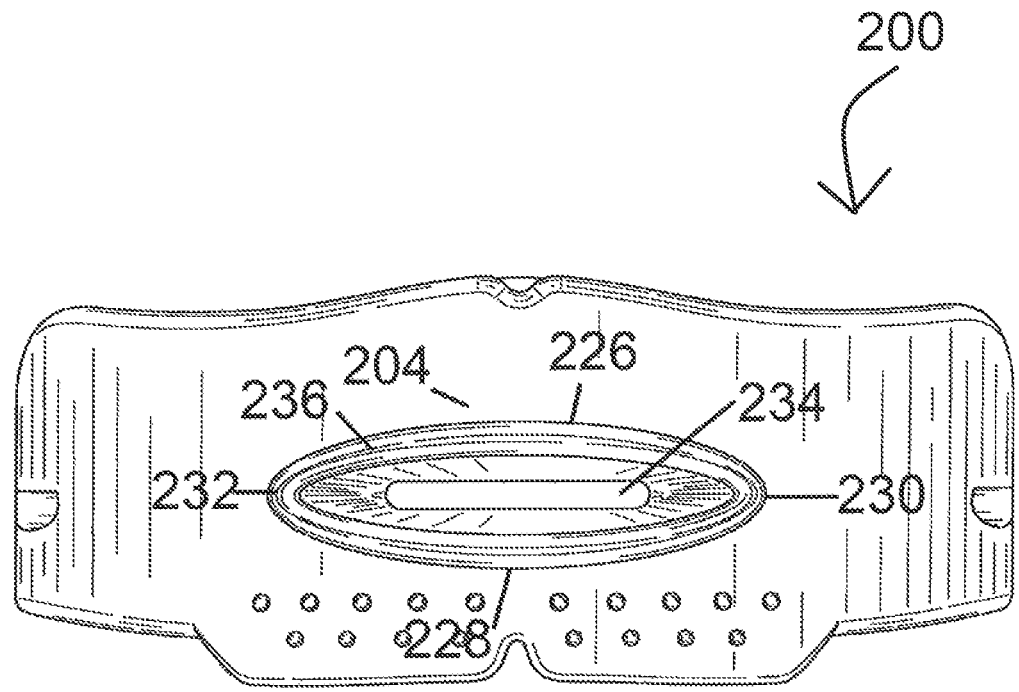
Figure 16:
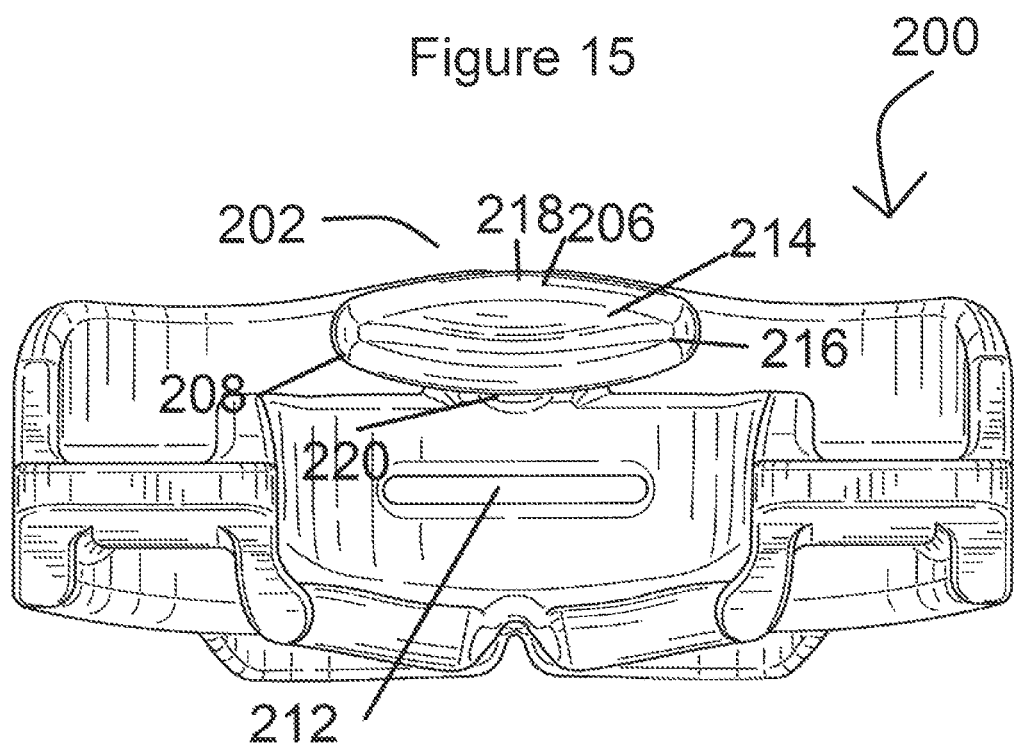
Figure 17:
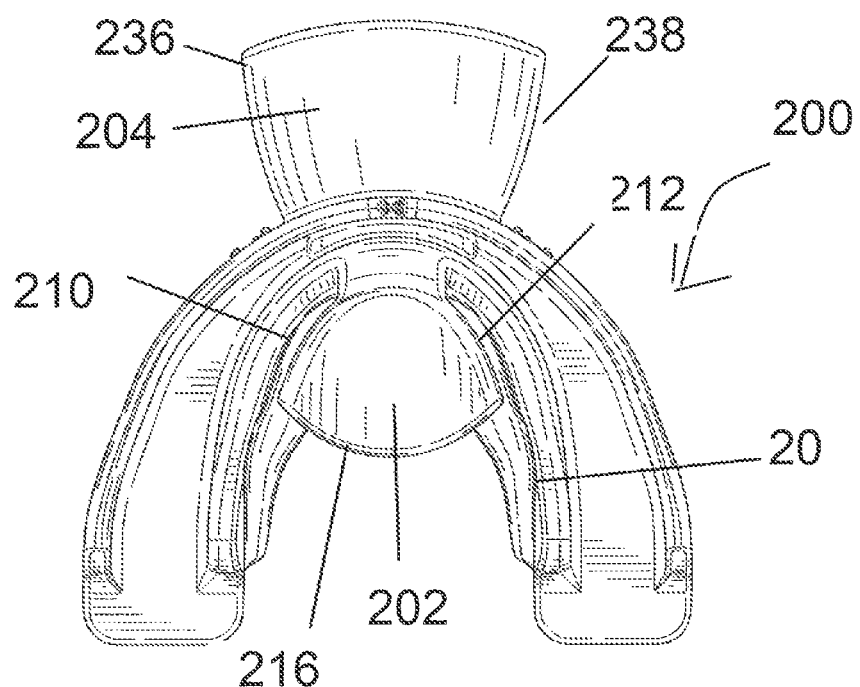
Figure 18:
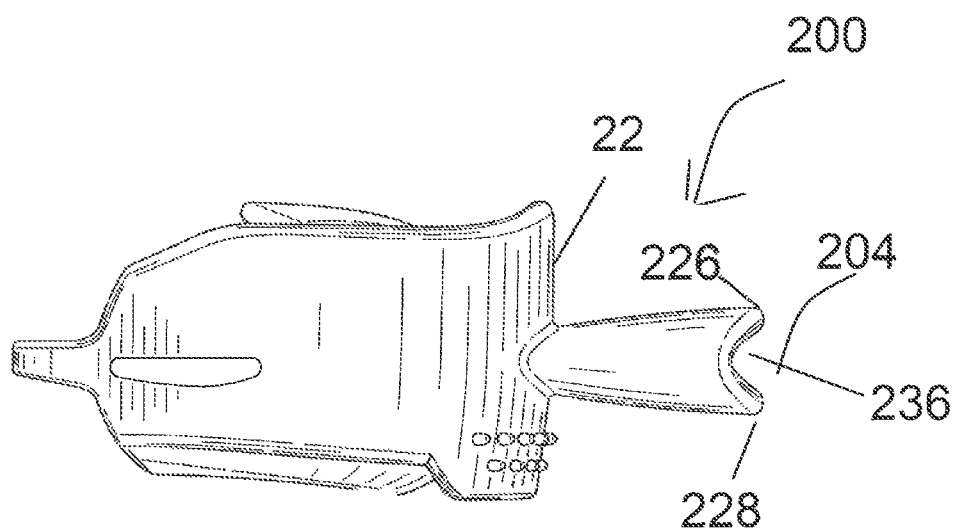
Figure 19:
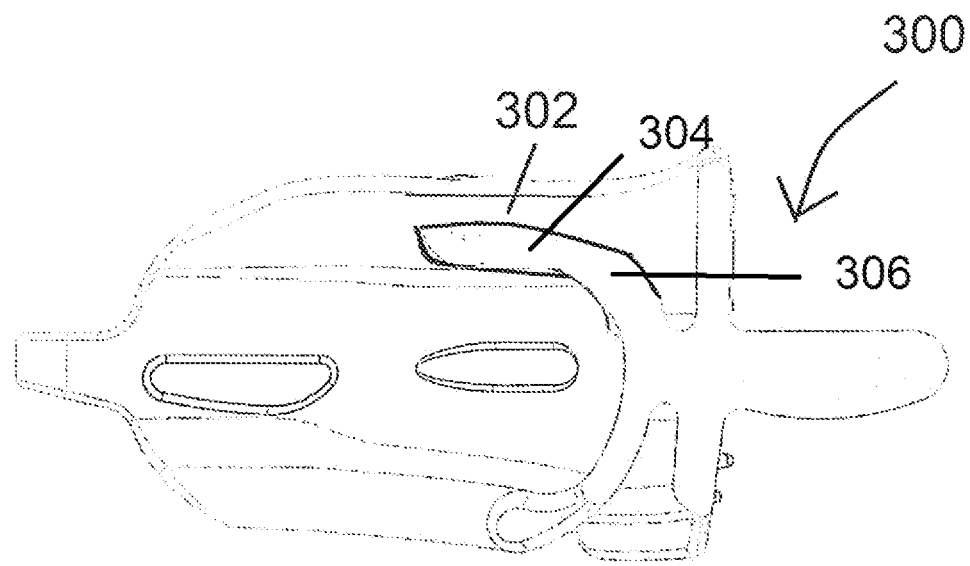
Figure 20:
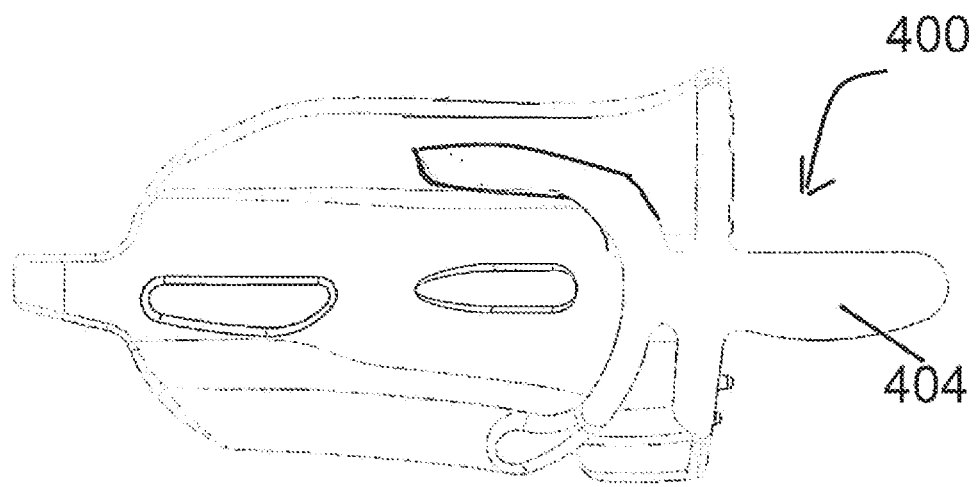

FIG. 3 is a front view of the appliance of FIG. 1;
FIG. 4 is a rear view of the appliance of FIG. 1;
FIG. 5 is a top plan view of the appliance of FIG. 1;
FIG. 6 is a bottom plan view of the appliance of FIG. 1;
FIG. 7 is a side view of the appliance of FIG. 1;
FIG. 8 is a sectional side view of the appliance of FIG. 1, the section being through the midline of the appliance;

FIG. 9 is a top perspective view of an appliance that is a variation on the appliance of configuration of the lip training member than shown in FIG. 1;

FIG. 10 is a rear perspective view of the appliance as shown in FIG. 9;

FIG. 11 is a front view of the appliance as shown in FIG. 9;

FIG. 12 is a rear view of the appliance as shown in FIG. 9;

FIG. 13 is front perspective view of an oral training appliance in accordance with a further embodiment of this disclosure;

FIG. 14 is a rear perspective view of the appliance of FIG. 13;

FIG. 15 is a front view of the appliance of FIG. 13;
FIG. 16 is a rear view of the appliance of FIG. 13;
FIG. 17 is a top plan view of the appliance of FIG. 13;
FIG. 18 is a side view of the appliance of FIG. 13;
FIG. 19 is a cross sectional side view of an oral training appliance in accordance with a further embodiment of this disclosure; and FIG. 20 is a cross sectional side view of an oral training appliance in accordance with a still further embodiment of this disclosure.

In FIGS. 1 to 8 reference numeral 10 refers generally to an oral training appliance in accordance with one embodiment of the disclosure.

The oral training appliance 10 includes a U shaped appliance body for mounting over the upper dental arch of a patient. The appliance 10 has a front portion 14 and two arms 16, 18 extending therefrom as clearly shown in FIGS. 5 and 6. The appliance body 12 is suitably formed from a flexible material such as silicone and is moulded in one piece.

The appliance body 12 includes a U shaped inner wall 20 that in use is positioned on a lingual side of the patient's dental arches and an outer wall 22 that is positioned on the facial and buccal sides of the dental arches.

The outer wall 22 has a front facial surface 22f and buccal side surfaces 22b. The buccal side surfaces 22b of the outer wall 22 serve to move or hold the cheeks away from the buccal aspect of the posterior teeth. This may protect the teeth from any force produced by the buccinators.

The appliance also includes a web 24 interconnecting the inner wall 20 and the outer wall 22 which lies between the dentition of the upper and the lower dental arches in use.

The inner wall 20 includes an upper portion 20u which projects up from the web 24 when the appliance 10 is mounted on the upper dental arch and a lower portion 20l which projects down from the web 24. Similarly the outer wall 22 comprises an upper portion 22u above the web 18 and a lower portion 22l below the web 24.

The inner wall 20, outer wall 22 and web 24 define upper and lower dental arch receiving channels 26 and 28 within which respectively the upper dental arch and the lower dental arch can be received.

The inner wall 20 has a lingual surface 32 and a channel surface 34. The outer wall 22 similarly has a channel surface 36.

The outer wall 22 has a lip bumper on the facial surface 22f thereof that is positioned below the web 24. The lip bumper comprises an array of dimple like protrusions 38 that may stretch and inactivate an overactive mentalis muscle.

The lower portion 20l of the inner wall 20 includes a tongue elevator 40. The inner wall 20 has a lower terminal edge region and the lower terminal edge region is thickened to form the tongue elevator 40. The tongue elevator 40 assists in keeping the tongue from resting within the lower dental arch adjacent the mandible.

A tongue training member 44 extends inwardly and substantially centrally in the upper portion 20u of the inner wall 20 corresponding to the midline of the patient's dentition and towards or adjacent the upper palette. The tongue training member 44 is integrally moulded with the appliance body 12.

The tongue training member 44 is not solid and has a transverse throughhole 46 defined by an upper wall 48 with an upper surface that is convex along the anteroposterior axis, a lower wall 50 having a lower surface that is concave along the anteroposterior axis and a curved rear or posterior wall 51 that is concave in the lateral axis.

The curvature of the upper surface is compatible with the corresponding convex surface of the upper palette of a user. This may be more clearly seen in the cross section shown in FIG. 8. This arrangement allows the tongue training member 44 to sit comfortably in the mouth and against the upper palate.

The concavity of the lower surface is complimentary to the upper surface of the tip of the tongue and allows the tip of the tongue to locate the correct point of contact.

The concavity of the rear wall 51 is also dimensioned to accommodate the tip of the tongue.

When the appliance 10 is placed in the mouth of a user that has an incorrect, lower tongue placement, the presence of the appliance within the mouth will stimulate oral somatosensory awareness and the tongue will haptically investigate the foreign object and the tongue tip will naturally find the lower surface of the tongue training member 44. Because the lower surface is curved so as to be complimentary to the shape of the tongue the tongue is comfortable in that position. The contact with the tongue training member 44 stimulates somatosensory awareness and assist in retraining the tongue to habitually locate against the palate when the appliance 10 is not being worn.

As the tongue training member 44 is formed from a flexible material, during such exploration, the tongue may push upwards on the lower surface 401, thereby moving it upwards so as to compress the throughole 46. The flexible material such as silicone is resilient and subject to elastic deformation such that the tongue training member is biased towards the rest position in which the throughole is in its resting configuration. The tongue will be naturally encouraged to find the correct position adjacent the upper palate.

The front section 14 of the outer wall 22 has a lip training member in the form of a projection 54 extending therefrom that in use will project between a user's upper and lower lips. The lip training member 54 has an upper wall 53 and a lower wall 55. The side view of FIG. 7 shows that the surface of the top wall is substantially flat and the surface of the lower wall 55 is concave in the anteroposterior axis. The lip training member has a throughole 56. The lip training member 54 is formed from a flexible and resilient material and is subject to elastic deformation. In use, a user can push the lower wall 55 upwards towards upper wall 48, compressing throughole 56.

In use a patient will be instructed to compress and release the lips against the bias of the lip training member 54. Suitably the patient will do sets of lip compression exercises against the bias of the lip training member 54.

The appliance 10 has two breathing holes 60, in the front section 14 and air spring cushion holes 62 towards the free ends of each arm 16, 18. The breathing holes 60 allow a patient to breathe through the mouth between sets of exercises. This provides a mouth breathing patient with a degree of confidence when wearing the appliance. If mouth breathing is blocked completely, the patient may panic and want to open their mouth. Further in severe cases of malocclusion, nasal breathing may be inhibited by a compromised maxilla that reduces the nasal passages.

When the patient compresses the lips together, the lips close over breathing holes 60 form a lip seal about the lip training member.

Patients with incompetent lips often compensate by using the mentalis muscle to raise the lower lips, thereby causing strain. The lip bumpers may alleviate this strain.

In view of the tongue begin the correct position and manipulation of the tongue training member 44 producing the suction, this suction assist in lip seal and there is less strain on the mentalis, allowing the lip seal position to be maintained longer.

The patient may be asked to swallow with the tongue in position and lip seal. This provides further training for tongue position.

The appliance 10 is kept in place by being held between the teeth with the mouth closed and the patient is told to keep the mouth closed and breathe through the nose. Keeping the mouth closed is important for a number of reasons. The correct resting position of the tongue requires the mouth to be closed. Further, closing the mouth encourages nasal breathing. Open mouth breathing is an oral habit resulting from or contributing to a number of oral defects. Still further if the mouth is open, the lip trainer and the side buccal surfaces cannot carry out their intended function in an optimal manner.

The appliance can be fitted in the mouth and removed from the mouth at will by a patient. It is not permanently fitted to the upper arch. It can therefore be fitted in a patient's mouth and removed from the mouth by a patient at will depending on lifestyle needs and considerations.

FIGS. 9 to 12 show another oral training appliance 100 as disclosed herein. The same reference numerals will be used to refer to the same components as in FIG. 1 unless otherwise indicated. The following description will focus on the differences between this appliance and the FIG. 1 appliance.

The appliance 100 has the same inner 20 and outer wall 22 arrangement and tongue training member 44 as that shown in FIG. 1. The main difference compared to the appliance 10 as shown in FIGS. 1 to 8 is the configuration of the lip training member 154 and the web 124.

As can be seen in FIGS. 9 to 12, the web 124 has a front breathing hole 112. The lip training member 154 is oval in cross section with an upper wall 155, a lower wall 153 and that defines a breathing passage 114 that is in fluid communication with the breathing hole 112 such that a person wearing the appliance can breathe through the breathing hole 112 with the lips at rest.

The patient is told to do sets of lip compression exercises in which the upper 155 and lower walls 153 are urged together, thereby compressing the breathing passage 114. It will be appreciated that there is a synergistic relationship between the lip compression and the correct tongue position and movement as dictated by the tongue training member.

As the person's lips become stronger, they are able to further compress the breathing passage, thereby encouraging nasal breathing.

The appliance 100 also has three air holes 120 towards the free end of each arm 16, 18.

FIGS. 13 to 18 show a further embodiment of the disclosed oral appliance 200. This appliance has the same basic structure with respect to the arrangement of the inner wall 20 and outer wall 22. The same reference numerals are used to refer to the same components. The main difference is in the configuration of the tongue training member 202 and the lip training member 204.

The tongue training member 202 has an upper wall 206, a lower wall 208 and opposed side edges 210, 212 that define a cavity 214 having a posteriorly facing opening 216 with an upper edge 218 and a lower edge 220. As can be best seen in FIG. 17, the side edges 210, 212 are arcuate and curve inwardly towards the front of the inner wall 20. The edges 218 and 220 are convex. The upper and lower walls 210, 212 are also curved as best seen in FIG. 13. The curvature of the upper wall 206 is complimentary to a user's palate so as to fit comfortably in the mouth. The curved edges define a smooth surface for the tongue.

The cavity 214 narrows in width from the opening 216 towards the inner wall 20 and also decreases in height towards the inner wall. The cavity 214 is configured so as to comfortably receive the tip of the tongue. As discussed above, the tongue will actively engage an object in the mouth. In this way, the appliance teaches the tongue to be in the correct position.

The tongue training member 202 is flexible with a degree of resiliency such that a user can push upwardly on the lower wall 208 towards the upper wall 206. When pressure is released, the tongue training member returns to the rest position.

The lip training member 204 has an upper wall 226, a lower wall 228 and opposed side edges 230, 232 that define a breathing passage 234 having a front facing opening 236 with an upper edge 238 and a lower edge 240. The upper and lower walls 226, 228 taper towards the outer wall 20, as best shown in FIG. 18. The lip training member 204 may even completely close off the opening in some exercises.

As can be best seen in FIG. 17, the side edges 230, 232 are tapered towards the outer wall 22. The edges 228 and 222 are convex. The upper 226 and lower walls 228 are also curved as best seen in FIG. 18.

The lip training member is operated as discussed above in that a user uses the lower lip to push the lower wall 228 towards the upper wall 226.

FIG. 19 shows a still further embodiment that has a further aspect of a tongue training member 302. The tongue training member 302 has a tab part 304 connected to the inner wall 20 by a hinge part 306. The tongue training member 302 is shown in the rest position. In use a user pushes the tab part 304 upwardly about the hinge part 306 towards the upper palette.

FIG. 20 shows a still further aspect 400 in which the lip training member is a compressible sold member.

In SDB, the tongue falls back and blocks or partially blocks the airway. Symptoms may be alleviated by bringing the tongue forward. As discussed above, the tongue will naturally find its way to the tongue training member, thereby bringing it forward. The tongue may also be brought further forward by advancing the mandible as is known in prior art snoring appliances.

The person will wear the appliance during the day so as to carry out the tongue, lip and swallowing exercise.

It will of course be realized that the above has been given only by way of illustrative example of the invention and that all such modifications and variations thereto, as would be apparent to persons skilled in the art, are deemed to fall within the broad scope and ambit of the invention as is herein set forth.

The invention claimed is:

1. An oral training appliance for training the tongue and lips of a person, the oral training appliance comprising;
   a U shaped appliance body comprising a front section and two arms, the appliance body comprising an inner wall and an outer wall;
   a web interconnecting the inner wall and the outer wall so as to define an upper dental arch receiving channel;
   a tongue training member configured in use to extend posteriorly from the inner wall and locate above the tongue and that is moveable in response to upwards movement by the user's tongue from a rest configuration to a training configuration and the tongue training member is biased towards the rest configuration; and
   a lip training member extending forwardly of the front section and is configured in use to extend between the person's lips, and is moveable in response to movement of a user's lower lip from a rest configuration to a training configuration and the lip training member is biased towards the rest configuration, wherein the lip training member has an upper wall and a lower wall that defines a breathing passage so as to allow breathing through the lip training member.

2. The oral training appliance of claim 1, wherein the tongue training member has an upper wall and a lower wall defining a cavity with a posterior facing opening.

3. The oral training appliance of claim 2, wherein an upper surface of the upper wall of the tongue training member is configured for compatibility with the upper palate.

4. The oral training appliance of claim 3, wherein, a lower surface of the lower wall of the tongue training member is concave so as to define a surface for comfortable receipt of the tip of the tongue.

5. The oral training appliance of claim 1, wherein the tongue training member comprises a tab member and a connecting member for connecting to the inner wall by a hinge part.

6. The oral training appliance of claim 5, wherein when the tab member is in the rest configuration it is spaced a distance below the user's hard palette.

7. The oral training appliance of claim 6, wherein upward movement of the tongue on the tab member pushes the tab member towards the person's upper palette.

8. The oral training appliance of claim 1, wherein the lip training member is configured such that when the lip training member is in the training configuration the breathing passage has a smaller cross sectional area for breathing than in the rest position.

9. The oral training appliance of claim 8 wherein the inner wall and the outer wall each have a lower portion that depends from the web so as to define a lower dental arch receiving channel.

10. The oral training appliance of claim 9, wherein the lower portion of the outer wall comprises a lip bumper and the lower part of the inner wall comprises a tongue elevator.

11. The oral training appliance of claim 1, wherein the tongue training member is a resilient plastics material formed integrally with the appliance body and the bias towards the rest configuration is provided by elastic deformation of the plastics material.

12. The oral training device of claim 11, wherein the elastic limit of the plastics material is greater than 60 kPa.

13. A method for oral training comprising providing the oral training device of claim 1 causing the user to wear the appliance whilst actuating the tongue training member with the tongue and actuating the lip training member with the lips.

14. The method of claim 13, wherein the user is instructed to practice compressing the tongue training member, generating excess saliva, swallowing with the tongue in position and the user is instructed to practice compressing the lip training member either separately or in conjunction with manipulation of the tongue training member.

15. The method of claim 13 wherein the tongue strength of a user will be periodically monitored during the treatment.

* * * * *